United States Patent [19]

Obermeier et al.

[11] Patent Number: 5,466,666
[45] Date of Patent: Nov. 14, 1995

[54] AMORPHOUS MONOSPHERIC FORMS OF INSULIN DERIVATIVES

[75] Inventors: Rainer Obermeier, Hattersheim; Walter Sabel, Bad Camberg; Peter Deil; Karl Geisen, both of Frankfurt am Main, all of Germany

[73] Assignee: Hoechst Aktiengesellschaft, Frankfurt am Main, Germany

[21] Appl. No.: 233,617

[22] Filed: Apr. 25, 1994

[30] Foreign Application Priority Data

Apr. 27, 1993 [DE] Germany ............... 43 13 702.4

[51] Int. Cl.$^6$ .................... A61K 38/28; C07K 14/62
[52] U.S. Cl. .................................. 514/3; 530/303
[58] Field of Search ................... 530/303; 514/3

[56] References Cited

U.S. PATENT DOCUMENTS 5,015,728  5/1991  Obermeier et al. ............ 530/303

FOREIGN PATENT DOCUMENTS

| | | |
|---|---|---|
| 0347781A2 | 12/1989 | European Pat. Off. . |
| 0368187A2 | 5/1990 | European Pat. Off. . |
| 0453969A1 | 10/1991 | European Pat. Off. . |
| WO91/03550 | 3/1991 | WIPO . |

OTHER PUBLICATIONS

Ruegg, V. T., Jarvis, D. Rudinger, J. (1979) *Biochem. J.* 179, 127–134 "2 Sulfobenzyl a new solubilizing and reversible . . .".

England, S. and Seifter, S. (1990) *Method Enzymol.* 182, 285–306 "Precipitation Techniques".

Y. Hu et al., "Crystallographic study on highly stable insulins–crystallization and preliminary crystallographic analysis of A21–Ser mutant," Chemical Abstracts, vol. 118, Nos. 11 (Mar. 1993) p. 97.

J. Markussen et al., "Prolonged–acting insulins, stable in acid solution. Crystallizability and biological potency of insulins substituted in positions A21, B27 and B30," chemical abstracts, vol. 114, No. 25 (Jun. 1991) p. 140.

A. Bialobrzeska et al., "Effect of crystallization parameters on the quality of insulin," chemical abstracts, vol. 97, No. 10 (Sep. 1982) pp. 414–415.

David S. Scott, "CCXI. Crystalline Insulin" Biochemical Journal, vol. XXVIII, No. 4, 1592–1603 (Apr. 1934).

Y. Hu et al., "Crystallographic study on highly stable insulins–crystallization and preliminary crystallographic analysis of A21–Ser mutant," Chemical Abstracts, vol. 118, Nos. 11 (Mar. 1993) p. 97.

J. Markussen et al., "Prolonged–acting insulins, stable in acid solution. crystallizability and biological potency of insulins substituted in positions A21, B27 and B30," chemical abstracts, vol. 114, No. 25 (Jun. 1991) p. 140.

*Primary Examiner*—Jill Warden
*Assistant Examiner*—Benet Prickril
*Attorney, Agent, or Firm*—Finnegan, Henderson, Farabow, Garrett & Dunner

[57] ABSTRACT

A process for the production of an amorphous monospheric form of insulin derivatives is described, wherein the insulin derivative is dissolved in an n-propanol/buffer mixture at a pH of 4.5 to 6.5, an n-propanol content of more than 13% relative to water is established and the resulting solution is subsequently diluted with water.

8 Claims, No Drawings

AMORPHOUS MONOSPHERIC FORMS OF INSULIN DERIVATIVES

Insulin is a polypeptide made up of 51 amino acid residues. The so-called A (acidic) chain consists of 21 amino acid residues, the B (basic) chain of 30 amino acid residues. In the native molecule the two chains are linked by 2 cystine bridges. There is a further disulfide bridge in the A chain between the cysteine residues at positions 6 and 11.

Since the work of D.A. Scott (Biochem. J.,(1934), 28, 1592) methods for the crystallization of insulins have been known. Addition of $Zn^{2+}$ ions to the customary crystallization buffers results in insulin preferentially forming a rhombohedral crystal form at its isoelectric point of pH 5.4. The unit cell contains a hexameric insulin that complexes 2 $Zn^{2+}$ ions.

Insulin isolated from humans, pigs or cattle is easily crystallizable on a preparative scale, while some insulin derivatives such as, for example, di-Arg-(B31–32)-human insulin can be crystallized only in the presence of phenol.

During the production and purification of insulin derivatives it is often necessary to isolate the purified material without the addition of phenol, so that the preparation of pharmaceutical formulations is not adversely affected. For preparative purposes an isoelectric precipitation followed by centrifugation and lyophilization is suitable for this insulin derivative. This leads to the formation of a fluffy insulin lyophilisate which is difficult to handle and like all lyophilized proteins is difficult to dose because of its hygroscopic behavior.

The object of the present invention was to develop a process with which insulin derivatives which are hard to crystallize can be separated in solid form.

A process has now been found which allows insulin derivatives to be isolated from solutions, which process comprises A) the insulin derivative being dissolved in an n-propanol/buffer mixture in which the n-propanol content relative to water is more than 15% and the pH is from 4.5 to 6.5, and B) the resulting solution being diluted with water so that the n-propanol content relative to water is less than 15%, whereupon an insulin derivative which is in an amorphous monospheric form as shown by Debye-Scherrer X-ray analysis precipitates out of the solution.

Surprisingly, the insulin derivatives produced in this manner show an amorphous monospheric form with an average diameter of about 5 µm. These insulin derivatives produced in this manner can be isolated from a suspension by filtration or by centrifugation, are stable in the dried state and can also be used as stable suspension in appropriate formulations.

In addition the invention relates to an amorphous monospheric form of the insulin derivatives, obtainable when A) the insulin derivative is dissolved in an n-propanol/buffer mixture in which the n-propanol content relative to water is more than 15% and the pH is from 4.5 to 6.5, and B) the resulting solution is diluted with water so that the n-propanol content relative to water is less than 15%, whereupon an insulin derivative which is in an amorphous monospheric form as shown by Debye-Scherrer X-ray analysis precipitates out of the solution.

Preferred insulin derivatives have the formula I

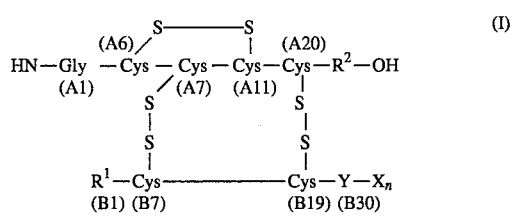

in which

X is a genetically encodable amino acid residue, n is an integer from 1 to 10,

Y is a genetically encodable amino acid residue, $R^1$ is a phenylalanine residue or a hydrogen atom, $R^2$ is a genetically encodable amino acid residue and the residues A2 –A20 correspond to the amino acid sequence of the A chain of human insulin, animal insulin or an insulin derivative, and the residues B2–B29 correspond to the amino acid sequence of the B chain of human insulin, animal insulin or an insulin derivative.

Preferred insulin derivatives have the formula I, in which

X is an Arg or Lys amino acid residue, n is an integer 1 or 2,

Y is an Ala, Thr or Ser amino acid residue, $R^z$ is the Phe amino acid residue, $R^2$ is an Asn, Ser or Gly amino acid residue, and the residues A2–A20 and B2–B29 correspond to the amino acid sequence of the A and B chains of human insulin.

Particularly preferred insulin derivatives have the formula I, in which

X is an Arg or Lys amino acid residue, n is an integer 1 or 2,

Y is the Thr amino acid residue, $R^1$ is the Phe amino acid residue, $R^2$ is the Asn or Gly amino acid residue, and the residues A2–A20 and B2–B29 correspond to the amino acid sequence of the A and B chains of human insulin.

The amino acid sequence of peptides and proteins is numbered starting from the N-terminal end of the amino acid chain. The entries shown in parentheses, e.g. A6, A20, B1, B7, B19 or B30, in formula I correspond to the position of amino acid residues in the A or B chains of insulin.

The term "genetically encodable amino acid residue" represents the amino acid residues Gly, Ala, Ser, Thr, Val, Leu, Ile, Asp, Asn, Glu, Gln, Cys, Met, Arg, Lys, His, Tyr, Phe, Trp, Pro and selenocysteine.

The terms "residues A2–A20" and "residues B2–B29" of animal insulin mean for example the amino acid sequences of insulin from cattle, pigs or chickens. The term residues A2–A20 and B2–B29 of insulin derivatives represents the corresponding amino acid sequences of human insulin formed by the exchange of amino acids for other genetically encodable amino acids.

The A chain of human insulin has the following sequence (Seq Id No. 1): Gly, Ile, Val, Glu, Gln, Cys, Cys, Thr, Ser, Ile, Cys, Ser, Leu, Tyr, Gln, Leu, Glu, Asn, Tyr, Cys, Asn The B chain of human insulin has the following sequence (Seq Id No. 2): Phe, Val, Asn, Gln, His, Leu, Cys, Gly, Ser, His, Leu, Val, Glu, Ala, Leu, Tyr, Leu, Val, Cys, Gly, Glu, Arg, Gly, Phe, Phe, Tyr, Thr, Pro, Lys, Thr The insulin derivative of the formula I can be formed in microorganisms with the aid of a large number of genetic engineering constructs (EP 0 489 780, EP 0 347 781, EP 0

368 187, EP 0 453 969). The genetic engineering constructs are expressed in microorganisms such as Escherichia coli or Streptomyces during fermentation. The proteins formed accumulate inside the microorganisms (EP 0 489 780) or are excreted into the fermentation solution.

Insulin derivatives of the formula I can be used for the process according to the invention in prepurified form, for example, after a precipitation or after a chromatographic purification.

The procedure for process step A) is the following:

The insulin derivatives are dissolved in n-propanol/buffer mixture to a concentration of 1%.

The n-propanol content, relative to water, is more than 15%, preferably 25 to 70%, in particular 40 to 60%.

The pH of the n-propanol buffer mixture is kept constant by the buffer. Suitable buffer substances are, for example, glycine/acetic acid/ammonium sulfate buffer. However, other substances may also be present in the buffer, as required for chromatographic processes for purification of the insulin derivatives, such as glycine, glutamine or betaine. The concentration of the buffer components may vary within wide limits; concentrations from 0.01 to 0.5M are preferred.

In addition, $Zn^{2+}$ ions may optionally be present 0.1 to 1.0% $ZnCl_2$ may be added, preferably from 0.3 to 0.5%.

For process step B), the solution obtained from A) is diluted with water or buffer. The n-propanol content should be less than 15% after the dilution, preferably to 12%. The diluted solution is stirred slowly at room temperature for 1 to 5 hours, preferably 2 to 3 hours, the amorphous monospheric form of the insulin derivatives precipitating out of the solution. The suspension can then be stored at 4° C. for 12 to 16 hours.

The monospheric insulin derivative sediments during this. After checking the clear supernatant for the absence of the insulin derivative, the supernatant is decanted and the concentrated suspension is then centrifuged, the precipitate is washed with a little water and dried or lyophilized in vacuo at 0° C.

The n-propanol-containing buffer solution of the insulin derivative is prepared by dissolving the solid product obtained by any method in the above buffer to a concentration of 0.5 to 1.7 %, preferably 1%.

Preferred for the isolation and chromatographic purification of the insulin derivatives is the use of appropriately suitable buffers which contain propanol, because this allows an immediate precipitation of the form, according to the invention, of the insulin derivatives.

The insulin derivatives according to the invention, as well as the corresponding pharmaceutical preparations containing these insulin derivatives, are suitable for the treatment of diabetes mellitus.

In the following examples the process according to the invention is described in detail. Percentages are based on weight unless otherwise stated.

EXAMPLE 1

Preparation of amorphous, monospheric Gly-A21-di-Arg(B31–32)-human insulin

Insulin derivative 1 with the following amino acid sequence is produced by fermentation of genetically modified Escherichia coli cells (EP 0 368 187): Insulin 1 (Seq Id No. 3):

Phe Val Asn Gln His Leu Cys Gly Ser His Leu Val Glu Ala Leu Tyr Leu Val Cys Gly Glu Arg Gly Phe Phe Tyr Thr Pro Lys Thr Arg Arg Gly Ile Val Glu Gln Cys Cys Thr Ser Ile Cys Ser Leu Tyr Gln Leu Glu Asn Tyr Cys Gly

Insulin 1 corresponds to the formula I, in which

X is Arg-Arg n is the number 2,

Y is Thr (B30), $R^1$ is Phe (B1), $R^2$ is Gly (A21) and

A2–A20 is the amino acid sequence of the A chain of human insulin (amino acid residues 2 to 20) and B2–B29 is the amino acid sequence of the B chain of human insulin (amino acid residues 2 to 29).

50 g of unpurified insulin 1 are dissolved in 3.3 l of a solution of 0.1M glycine, 0.05M $(NH_4)_2SO_4$, 0,025M acetic acid and 50% n-propanol at pH 5.5 and diluted with 3.3 l of buffer A (0.2M ammonium sulfate, 0.1M glycine, 0,025M acetic acid, 5% n-propanol in water, pH 5.5). The resulting mixture is diluted with water to a propanol content of less than 10% and 0.4% $ZnCl_2$, relative to total volume of the solution, is added. The pH of the solution is checked and if required adjusted with a few drops of 1N NaOH to pH 5.5. The solution is stirred slowly at room temperature, resulting in the product in the desired form. To complete the precipitation the solution is stored at cold-room temperature overnight. After sedimentation of the product the clear supernatant is decanted off. The sediment is centrifuged. The moist monospheric Gly-A21-di-Arg-(B31–32)-human insulin thus obtained is washed with water to remove any adherent buffer and then dried under reduced pressure at 0° C. Yield: 36 g.

EXAMPLE 2

Preparation of monospheric di-Arg-(B31–32)-human insulin

An insulin derivative 2 with the following amino acid sequence is produced by fermentation of genetically modified Escherichia coli cells in the same manner as for Example 1. Insulin 2 (Seq Id No. 4):

Phe Val Asn Gln His Leu Cys Gly Ser His Leu Val Glu Ala Leu Tyr Leu Val Cys Gly Glu Arg Gly Phe Phe Tyr Thr Pro Lys Thr Arg Arg Gly Ile Val Glu Gln Cys Cys Thr Ser Ile Cys Ser Leu Tyr Gln Leu Glu Asn Tyr Cys Asn

Insulin 2 corresponds to the formula I, in which

X is Arg-Arg n is the number 2,

Y is Thr (B30), $R^1$ is Phe (B1), $R^2$ is Asn (A21) and

A2–A20 is the amino acid sequence of the A chain of human insulin (amino acid residues 2 to 20) and B2–B29 is the amino acid sequence of the B chain of human insulin (amino acid residues 2 to 29).

1 g of di-Arg-(B31–32)-human insulin is dissolved in 100 ml of buffer B and the solution is sterilized by filtration. The filtrate is diluted with 100 ml of sterile buffer A and 350 ml of sterile water and stirred with a paddle stirrer for 3 hours at room temperature. To complete the sedimentation the suspension is stored at 4° C. for 14 hours. The monospheric insulin derivative thus obtained is removed by centrifugation and the precipitate is washed to remove any adherent buffer and lyophilized. Yield: 0.87 g.

Buffer A: 0.2M $(NH_4)_2SO_4$/0M glycine/0.025M acetic acid in 5% aqueous n-propanol/pH 5.5

Buffer B: 0.05M $(NH_4)_2SO_4$/0.1M glycine/0.025M acetic acid in 50% aqueous n-propanol pH 5.5

EXAMPLE 3

Production of a GLY-A21-di-Arg-(B31–32)-human insulin preparation 14.8 mg of GLY-A21-di-Arg-(B31–32)-human insulin (monospheric, corresponding to Example 1), produced under sterile conditions, are suspended under sterile conditions in 10 ml of a placebo buffer for insulin preparations (pH 7). To check the stability the suspension was shaken for 1 week at 4° C. on a shaker at 100 Hz. Microscopic examination of the spherical form showed no changes. Chromatographic investigation of the clear supernatant after centrifugation revealed less than 1% insulin in the solution.

In order to test the blood sugar-lowering effect of the above insulin derivative some of the preparation was first transformed into a clear solution by acidifying to pH 4.5. Intravenous administration (0.2 IU/kg) to a dog showed a reduction in blood sugar comparable to that of an equimolar dose of human insulin. Subcutaneous administration of the suspension showed at first only a slight but long-lasting reduction in blood sugar, which after repeated injection showed a basal profile.

---

We claim:

1. An amorphous monospheric form of an insulin derivative, obtained by

A) dissolving an insulin derivative in an n-propanol/buffer mixture in which the n-propanol content relative to water is more than 15% and the pH is from 4.5 to 6.5, forming a solution and B) diluting the solution with water so that the n-propanol content relative to water is less than 15%, whereupon the insulin derivative precipitates out of the solution in an amorphous monospheric form wherein the insulin derivative that is used has an A chain and a B chain and is of the formula I

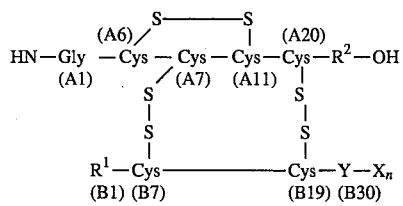

(I)

in which

X is a genetically encodable amino acid residue, n is an integer from 1 to 10,

Y is a genetically encodable amino acid residue, $R^1$ is a phenylalanine residue or a hydrogen atom, $R^2$ is a genetically encodable amino acid residue and residues A2–A20 correspond to the amino acid sequence of the A chain of human insulin, animal insulin or an insulin derivative, and residues B2–B29 correspond to the amino acid sequence of the B chain of human insulin, animal insulin or an insulin derivative.

2. An amorphous monospheric form of an insulin derivative as claimed in claim 1, wherein an insulin derivative of the formula I, in which X is an Arg or Lys amino acid residue, n is an integer 1 or 2, Y is the Ala, Thr or Ser amino acid residue, $R^1$ is the Phe amino acid residue, $R^1$ is the Asn, Ser or Gly amino acid residue, and the residues A2–A20 and B2–B29 correspond to the amino acid sequence of the A and B chains of human insulin, is used.

3. A amorphous monospheric form of an insulin derivative as claimed in claim 1, wherein an insulin derivative of the formula I, in which X is an Arg or Lys amino acid residue, n is an integer 1 or 2, Y is the Thr amino acid residue, $R^1$ is the Phe amino acid residue, $R^2$ is the Asn, or Gly amino acid residue, and the residues A2–A20 and B2–B29 correspond to the amino acid sequence of the A and B chains of human insulin, is used.

4. A process for the production of an amorphous, monospheric form of an insulin derivative as defined in claim 1, which comprises A) dissolving the insulin derivative in an n-propanol/buffer mixture in which the n-propanol content relative to water is more than 15% and the pH is from 4.5 to 6.5, to form a solution and B) diluting the solution with water so that the n-propanol content relative to water is less than 15%, whereupon an insulin derivative which is in an amorphous monospheric form as shown by Debye-Scherrer X-ray analysis precipitates out of the solution.

5. The process as claimed in claim 4, wherein the propanol concentration after the dilution is 5 to 12%.

6. The process as claimed in claim 4, wherein a buffer containing glycine, ammonium sulfate and acetic acid is used.

7. A pharmaceutical composition, containing the amorphous monospheric form of an insulin derivative as claimed in claim 1 and a physiologically tolerated vehicle.

8. A method of treating diabetes mellitus comprising administering an effective amount of the pharmaceutical composition of claim 7.

* * * * *

UNITED STATES PATENT AND TRADEMARK OFFICE
CERTIFICATE OF CORRECTION

PATENT NO. : 5,466,666
DATED : November 14, 1995
INVENTOR(S) : Rainer OBERMEIER et al.

It is certified that error appears in the above-indentified patent and that said Letters Patent is hereby corrected as shown below:

In Claim 2, Column 8, line 42, "$R^1$ is the ASN," should read --$R^2$ is the ASN,--.

In Claim 3, Column 8, line 47, "A amorphous" should read --An amorphous--.

Signed and Sealed this

Twenty-fourth Day of September, 1996

Attest:

BRUCE LEHMAN

Attesting Officer    Commissioner of Patents and Trademarks

SEQUENCE LISTING ( 1 ) GENERAL INFORMATION:

( i i i ) NUMBER OF SEQUENCES: 4

( 2 ) INFORMATION FOR SEQ ID NO: 1:

( i ) SEQUENCE CHARACTERISTICS:
( A ) LENGTH: 21 amino acids
( B ) TYPE: amino acid
( D ) TOPOLOGY: linear ( i i ) MOLECULE TYPE: protein ( v i ) ORIGINAL SOURCE:
( A ) ORGANISM: Escherichia coli ( x i ) SEQUENCE DESCRIPTION: SEQ ID NO: 1:

```
Gly  Ile  Val  Glu  Gln  Cys  Cys  Thr  Ser  Ile  Cys  Ser  Leu  Tyr  Gln  Leu
1                   5                        10                       15
Glu  Asn  Tyr  Cys  Asn
                20
```

( 2 ) INFORMATION FOR SEQ ID NO: 2:

( i ) SEQUENCE CHARACTERISTICS:
( A ) LENGTH: 30 amino acids
( B ) TYPE: amino acid
( D ) TOPOLOGY: linear ( i i ) MOLECULE TYPE: protein ( v i ) ORIGINAL SOURCE:
( A ) ORGANISM: Escherichia coli ( x i ) SEQUENCE DESCRIPTION: SEQ ID NO: 2:

```
Phe  Val  Asn  Gln  His  Leu  Cys  Gly  Ser  His  Leu  Val  Glu  Ala  Leu  Tyr
1                   5                        10                       15
Leu  Val  Cys  Gly  Glu  Arg  Gly  Phe  Phe  Tyr  Thr  Pro  Lys  Thr
                20                        25                       30
```

( 2 ) INFORMATION FOR SEQ ID NO: 3:

( i ) SEQUENCE CHARACTERISTICS:
( A ) LENGTH: 53 amino acids
( B ) TYPE: amino acid
( D ) TOPOLOGY: linear ( i i ) MOLECULE TYPE: protein ( v i ) ORIGINAL SOURCE:
( A ) ORGANISM: Escherichia coli ( x i ) SEQUENCE DESCRIPTION: SEQ ID NO: 3:

```
Phe  Val  Asn  Gln  His  Leu  Cys  Gly  Ser  His  Leu  Val  Glu  Ala  Leu  Tyr
1                   5                        10                       15
```

```
            Leu  Val  Cys  Gly  Glu  Arg  Gly  Phe  Phe  Tyr  Thr  Pro  Lys  Thr  Arg  Arg
                           20                       25                      30

Gly  Ile  Val  Glu  Gln  Cys  Cys  Thr  Ser  Ile  Cys  Ser  Leu  Tyr  Gln  Leu
                                35                       40                      45

Glu  Asn  Tyr  Cys  Gly
                           50
```

( 2 ) INFORMATION FOR SEQ ID NO: 4:

( i ) SEQUENCE CHARACTERISTICS:
      ( A ) LENGTH: 53 amino acids
      ( B ) TYPE: amino acid
      ( D ) TOPOLOGY: linear ( i i ) MOLECULE TYPE: protein ( v i ) ORIGINAL SOURCE:
      ( A ) ORGANISM: Escherichia coli ( x i ) SEQUENCE DESCRIPTION: SEQ ID NO: 4:

```
            Phe  Val  Asn  Gln  His  Leu  Cys  Gly  Ser  His  Leu  Val  Glu  Ala  Leu  Tyr
            1                   5                        10                       15

Leu  Val  Cys  Gly  Glu  Arg  Gly  Phe  Phe  Tyr  Thr  Pro  Lys  Thr  Arg  Arg
                           20                       25                      30

Gly  Ile  Val  Glu  Gln  Cys  Cys  Thr  Ser  Ile  Cys  Ser  Leu  Tyr  Gln  Leu
                                35                       40                      45

Glu  Asn  Tyr  Cys  Asn
                           50
```